US010813652B2

(12) United States Patent
Muir et al.

(10) Patent No.: US 10,813,652 B2
(45) Date of Patent: Oct. 27, 2020

(54) OFFSET GUIDE

(71) Applicant: Biomet Manufacturing, LLC, Warsaw, IN (US)

(72) Inventors: Nicholas Muir, Winona Lake, IN (US); Michael Francis Kovacs, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 182 days.

(21) Appl. No.: 15/984,671

(22) Filed: May 21, 2018

(65) Prior Publication Data

US 2018/0338769 A1 Nov. 29, 2018

Related U.S. Application Data

(60) Provisional application No. 62/509,948, filed on May 23, 2017.

(51) Int. Cl.
| | | |
|---|---|---|
| *A61B 17/17* | (2006.01) | |
| *A61F 2/46* | (2006.01) | |
| *A61B 17/16* | (2006.01) | |
| *A61F 2/40* | (2006.01) | |
| *A61B 17/56* | (2006.01) | |

(52) U.S. Cl.
CPC ...... *A61B 17/1778* (2016.11); *A61B 17/1684* (2013.01); *A61F 2/4081* (2013.01); *A61F 2/4612* (2013.01); *A61B 2017/568* (2013.01)

(58) Field of Classification Search
CPC ............ A61B 17/1739; A61B 17/1778; A61B 17/1746; A61B 17/1684; A61F 2/4612
See application file for complete search history.

(56) References Cited

U.S. PATENT DOCUMENTS

| | | | | |
|---|---|---|---|---|
| 6,228,120 B1* | 5/2001 | Leonard | ................ | A61F 2/4684 |
| | | | | 623/19.12 |
| 10,548,617 B1* | 2/2020 | Olson | ................ | A61B 17/1617 |
| 2011/0029088 A1* | 2/2011 | Rauscher | ........... | A61B 17/1778 |
| | | | | 623/19.11 |

(Continued)

FOREIGN PATENT DOCUMENTS

| | | |
|---|---|---|
| CN | 100650694 A | 1/2020 |
| WO | WO-2011001292 A1 | 1/2011 |
| WO | 2018217608 | 11/2018 |

OTHER PUBLICATIONS

"International Application Serial No. PCT/US2018/033620, International Search Report dated Aug. 6, 2018", 5 pgs.

(Continued)

*Primary Examiner* — Matthew J Lawson
*Assistant Examiner* — Lisa Nguyen
(74) *Attorney, Agent, or Firm* — Schwegman Lundberg & Woessner, P.A.

(57) ABSTRACT

An offset guide can include a body, an arcuate portion, a first fin, and a second fin. The body can have a first surface. The arcuate portion can extend from the body and have a second surface. The first surface and the second surface can define an opening. The first fin can extend from the first surface into the opening. The second fin can extend from the first surface into the opening. A portion of the first surface can be located between the first fin and the second fin and arranged at an angle relative to a longitudinal axis of the offset guide.

11 Claims, 4 Drawing Sheets

(56) References Cited

U.S. PATENT DOCUMENTS

| | | | |
|---|---|---|---|
| 2014/0188231 A1* | 7/2014 | Poncet | A61F 2/4637 623/19.14 |
| 2014/0236160 A1* | 8/2014 | Barsoum | A61F 2/4657 606/91 |
| 2014/0257495 A1* | 9/2014 | Goldberg | A61F 2/4081 623/19.11 |
| 2016/0287266 A1 | 10/2016 | Sikora et al. | |
| 2018/0333263 A1* | 11/2018 | Roby | A61F 2/30734 |

OTHER PUBLICATIONS

"International Application Serial No. PCT/US2018/033620, Written Opinion dated Aug. 6, 2018", 10 pgs.

"International Application Serial No. PCT US2018 033620, International Preliminary Report on Patentability dated Dec. 5, 2019", 10 pgs.

"European Application Serial No. 18729313.9, Response to Communication pursuant to Rules 161(1) and 162 EPC filed Aug. 3, 2020", 38 pages.

* cited by examiner

OFFSET GUIDE

PRIORITY APPLICATIONS

This application claims the benefit of priority to U.S. Provisional Application Ser. No. 62/509,948, filed May 23, 2017, the content of which is incorporated herein by reference in its entirety.

FIELD OF THE DISCLOSURE

The present disclosure relates to surgical implant systems, including implants, instruments, and methods for installing an implant. Specifically, the present disclosure relates to systems and methods for implanting a reamer guide rod.

BACKGROUND

Surgical procedures for repairing or reconstructing a joint can require securely fastening a guide rod and other instruments to bone. For example, shoulder joint reconstruction can require attaching a guide rod to a scapula. Drills and hammers can be used to screw or drive the guide rod into the bone.

SUMMARY

To better illustrate the system disclosed herein, a non-limiting list of examples is provided here:

Example 1 includes an offset guide. The offset guide can include a body, an arcuate portion, a first fin, and a second fin. The body can have a first surface. The arcuate portion can extend from the body and have a second surface. The first surface and the second surface can define an opening. The first fin can extend from the first surface into the opening. The second fin can extend from the first surface into the opening. A portion of the first surface can be located between the first fin and the second fin and arranged at an angle relative to a longitudinal axis of the offset guide.

In Example 2, the offset guide of Example 1 can optionally include the angle being between about 5 degrees and about 20 degrees.

In Example 3, the offset guide of any one or any combination of Examples 1 and 2 can optionally include a tab extending from the arcuate portion into the opening, the tab defining an aperture.

In Example 4, the offset guide of Example 3 can optionally include the aperture including a threaded portion configured to receive an offset member.

In Example 5, the offset guide of Example 4 can optionally include the offset member being a bolt or a screw.

In Example 6, the offset guide of Example 4 can optionally include the offset member including a tip having a blunt profile.

In Example 7, the offset guide of any one or any combination of Examples 1-6 can optionally include the body including a third surface that is curved to match a profile of a glenoid implant.

In Example 8, the offset guide of any one or any combination of Examples 1-7 can optionally include the body defining a connection member configured to connect to a handle.

Example 9 includes an offset guide. The offset guide can include a body, a first fin, and a second fin. The body can have a longitudinal axis and a curved surface arranged at an angle relative to the longitudinal axis. The first fin can extend from the body. The second fin can extend from the body. The second fin can be parallel to the first fin. A channel sized to receive a guide rod can be defined between an inner surface of the first fin, an inner surface of the second fin, and the curved surface.

In Example 10, the offset guide of Example 9 can optionally include the angle being between about 5 degrees and about 20 degrees.

In Example 11, the offset guide of any one or any combination of Examples 9 and 10 can optionally include an arcuate portion and a plurality of tabs. The arcuate portion can extend from the body. The body and the arcuate portion can define an opening. The plurality of tabs can extend from the arcuate portion into the opening. Each of the plurality of tabs can define an aperture.

In Example 12, the offset guide of Example 11 can optionally include each of the apertures including a threaded portion configured to receive an offset member.

In Example 13, the offset guide of Example 12 can optionally include the offset member being a bolt or a screw.

In Example 14, the offset guide of Example 12 can optionally include the offset member including a tip having a blunt profile.

In Example 15, the offset guide of any one or any combination of Examples 9-14 can optionally include the body including a third surface that is curved to match a profile of a glenoid implant.

In Example 16, the offset guide of any one or any combination of Examples 9-15 can optionally include the body defining a connection member configured to connect to a handle.

Example 17 includes a system for preparing a glenoid to receive a glenoid implant. The system can include a guide rod, an offset guide, and a plurality of offset members. The offset guide can include a body, an arcuate portion, a plurality of tabs, a first fin, and a second fin. The body can have a first curved surface. The arcuate portion can extend from the body and have a second curved surface. The body and the second curved surface can define an opening. The plurality of tabs can extend from the second curved surface. Each of the plurality of tabs can define an aperture. The first fin can extend from the body into the opening. The second fin can extend from the body into the opening. The first curved surface can be located between the first fin and the second fin and arranged at an angle relative to a longitudinal axis of the offset guide. The first curved surface, the first fin, and the second fin can define a notch sized to receive the guide rod. Each of the plurality of offset members can be sized to be received by at least one of the apertures defined by the plurality of tabs.

In Example 18, the system of Example 17 can optionally include the angle being between about 5 degrees and about 20 degrees.

In Example 19, the system of any one or any combination of Examples 17 and 18 can optionally include the plurality of offset members being bolts and each of the apertures including a threaded portion configured to engage with one of the bolts.

In Example 20, the system of any one or any combination of Examples 17-19 can optionally include the body including a third surface that is curved to match a profile of the glenoid implant.

In Example 21, the system of any one or any combination of Examples 17-20 can optionally include a handle. The body and the handle can be configured to mate together.

In Example 22, the system of Example 21 can optionally include the body defining a first connection member and a second connection member located on an opposing side of the body. The handle can be configured to alternatively mate with the first connection member and the second connection member.

Example 23 includes a method for preparing a glenoid for reaming. The method can include placing an offset guide adjacent or proximate the glenoid, the offset guide including: a body having a first curved surface, an arcuate portion extending from the body and having a second curved surface, the body and the second curved surface defining an opening, a plurality of tabs extending from the second curved surface into the opening, a first fin extending from the body into the opening, and a second fin extending from the body into the opening, the first curved surface located in between the first fin and the second fin and arranged at an angle relative to a longitudinal axis of the offset guide, the first curved surface, the first fin, and the second fin defining a notch sized to receive a guide rod; adjusting at least one of a plurality of offset members to achieve a desired spacing between a portion of the glenoid and a portion of the offset guide, each of the plurality of offset members passing through a respective aperture defined by one of the plurality of tabs; passing the guide rod through the opening and into the glenoid such that a sidewall of the guide rod is in contact with the first curved surface.

In Example 24, the method of Example 23 can optionally include adjusting the at least one of the plurality of offset members including threading the at least one of the plurality of offset members into or out of the respective aperture.

In Example 24, the method of any one or combination of Examples 23 and 24 can optionally include selecting the offset guide from a plurality of offset guides. Each of the plurality of offset guides having a different size.

In Example 25, the method of any one or combination of Examples 22-25 can optionally include removing the offset guide while the guide rod remains in the glenoid.

In Example 26, the offset guide, systems, or methods of any one of or any combination of Examples 1-1-25 are optionally configured such that all elements or options recited are available to use or select from.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure any manner.

DETAILED DESCRIPTION

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves. In addition, the terms implant and prosthesis, and variations thereof, can be used interchangeably.

Through injury, trauma, aging, or other degenerative conditions a joint, such as the shoulder, can become damaged or otherwise less mobile. In addition, the injury, trauma, aging, or other condition can cause repeated injury. For example, an injury to a shoulder can cause a central detect or other damage to a glenoid. The damage can cause the humeral head to more easily become dislocated from the glenoid, limit range of motion, cause pain during motion, etc.

In some instances, the damage can be surgically repaired. For instance, an anatomical shoulder replacement can allow for a glenoid implant to be implanted within a glenoid and a humeral head to be replaced with a humeral implant. During the surgery, one or more guide rods may need to be temporarily implanted within the glenoid. The guide rod can provide stabilization and guidance for reamers that can shape the bone as well as remove damaged or diseased bone.

As disclosed herein, an offset guide can be used to properly position a guide rod. The offset guide can support the guide rod during placement. In addition, the offset guide can properly support the guide rod at an appropriate angle relative to a central axis of the offset guide or a face of a bone. For example, the offset guide can support the guide rod at an angle relative to a surface of a glenoid. The angle can be specific to the patient or the prosthetic to be implanted.

To achieve the angle, the offset guide can include a body that has a surface that is orientated at an angle relative to a reference (e.g., a central axis of the offset guide). During surgery, the guide rod can rest against the surface for support. The surface can be curved such that fins that project from the surface, or other surfaces of the body, form a notch sized to receive the guide rod.

In addition to the surface, the offset guide can include one or more tabs that extend from an arcuate portion. The arcuate portion can be connected to the body of the offset guide and define an opening through which the guide rod can pass. Each tab can operate with one or more offset members. The offset members can be adjustable such that a position of the offset guide relative to the bone can be adjusted on a per patient or per prosthetic basis.

Figure 1:
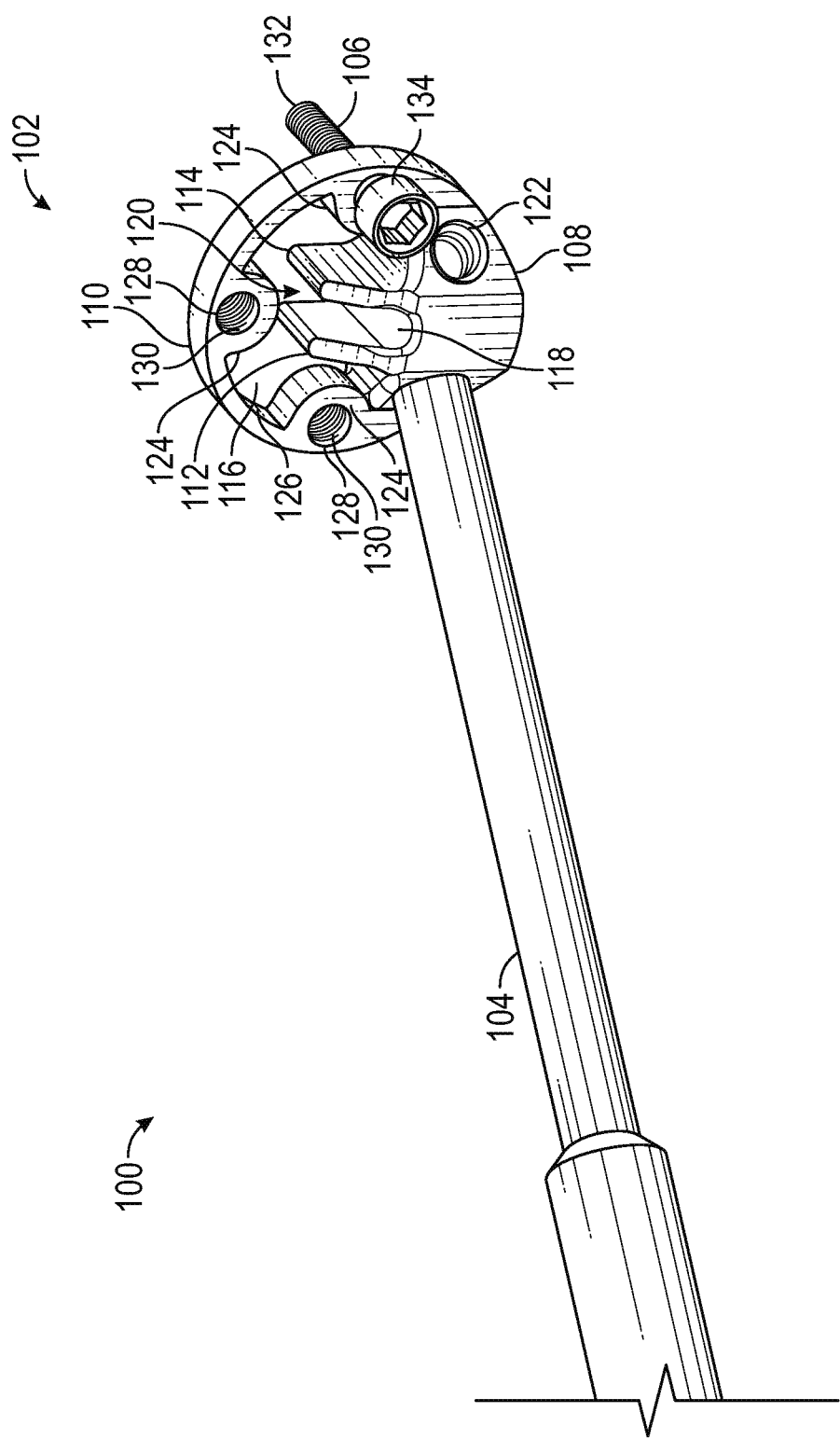
FIG. 1 shows a system in accordance with at least one example of the present disclosure.

FIG. 1 shows a system 100 in accordance with at least one example of the present disclosure. The system 100 can include an offset guide 102, a handle 104, and one or more offset members 106.

The offset guide 102 can include a body 108, an arcuate portion 110, a first fin 112, and a second fin 114. The arcuate portion 110 can extend from the body 108. The body 108 and the arcuate portion 110 can define an opening 116. The opening 116 can allow a surgeon to view a bone or surgical site, such as a scapula or glenoid.

The first fin 112 and the second fin 114 can extend from a first surface 118. The first surface 118 can be curved. The first fin 112, the second fin 114, and the first surface 118 can define a notch 120 through which a guide rod can rest. For example, and as disclosed herein, during a surgery, a surface of the guide rod can rest against the first surface 118.

Figure 2:
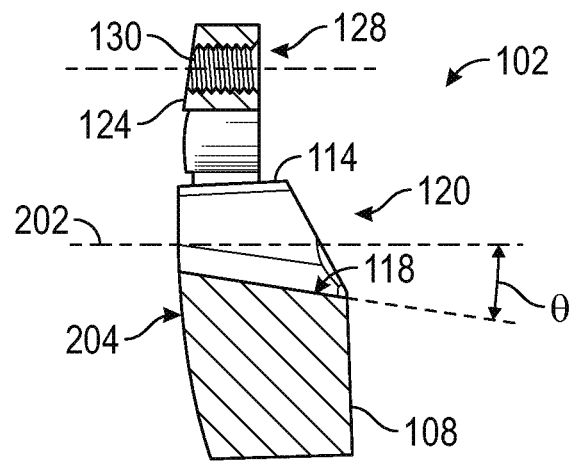
FIG. 2 shows a section view of an offset guide in accordance with at least one example of the present disclosure.

As shown in FIG. 2, the first surface 118 can be arranged at an angle θ relative to a longitudinal axis 202 of the offset guide 102. The angle θ can be from about 5° to about 20°. The angle θ can depend on the type, size, location, etc. of the guide rod to be implanted. In addition, the angle θ can depend on the type and size of prosthetic to be implanted. For example, the angle θ can be a first value for a 3.2 mm guide rod and can be a second value for a 2.7 mm guide rod. Depending upon the angle desired, a surgeon can select the offset guide 102 from a plurality of offset guides. Each of the plurality of offset guides can have a different angle θ.

The spacing between the first fin 112 and the second fin 114, as well as a curvature of the first surface 118 can depend on the size, type, location, etc. of the guide rod to be implanted. For example, for a 3.2 mm guide rod, the spacing between the first fin 112 and the second fin 114 may be 3 mm with a slight indentation in both the first fin 112 and the second fin 114 to help hold the guide rod in the notch 120. The radius of curvature of the first surface 118, as well as any indentations that can exist in the first fin 112 and the second fin 114, can be the radius of the guide rod.

The offset guide 102 can also include one or more tabs 124. The tabs 124 can be defined by the arcuate portion 110. For instance, as shown in FIG. 1, the tabs 124 can extend from a second surface 126 into the opening 116. Each of the tabs 124 can define an aperture 128 and the aperture 128 may include a threaded portion 130. The aperture 128 can receive the offset member 106. For example, the offset member 106 can be a bolt or screw that can be inserted into the aperture. As discussed in greater detail below, the threaded nature of the aperture and the offset member 106 can allow a surgeon to adjust a depth in which the offset member 106 spaces a third surface 204 (See FIG. 2) from a bone. The offset member 106 can include a blunt tip 132 that can rest against bone and minimize potential damage to the bone.

In addition, the system 100 can utilize offset members having different lengths. For example, a portion of a shank proximate a head 134 can be threaded while a remainder of the shank is unthreaded. Thus, a surgeon can secure the offset members 106 to the tabs 124 and have the tip 132 remain unthreaded. As a result, the tip 132 can be polished, rounded, etc. to minimize potential damage to the bone or surrounding tissues due to vibration created by the rotating guide rod.

Other methods can be used to secure the offset members 106 to the offset guide. For example, the arcuate portion 110 may include set screws that can pass through the arcuate portion 110 and contact the offset members 106 to secure the offset members 106 at a desired position.

The body 108 can define one or more connection members 122. The connection members 122 can be a threaded hole such that the handle 104 can attach to the body 108. In addition to threaded holes, the connection members 122 can be configured to allow a surgeon to snap fit, press fit, utilize a Luer lock, etc. to attach the handle 104 to the body 108. The handle 104 can attach to the body 108 at multiple locations to allow a surgeon to select an attachment point most convenient to the surgeon. For example, for use in repairing a patient's right shoulder, the surgeon may wish to attach the handle 104 to a right side of the body 108 and for repairing a patient's left shoulder, the surgeon may wish to attach the handle 104 to the left side of the body 108. Attaching the handle 104 at different locations can allow the surgeon to position the handle 104 such that an assistant can hold the handle 104 while the surgeon implants the guide rod.

Referring again to FIG. 2, the third surface 204 can be curved. The shape or radius of curvature of the third surface 204 can depend on the prosthetic to be implanted or the patient. For example, the third surface 204 can be curved to match a profile of a glenoid implant to be implanted. In addition, the third surface 204 can be curved to match a curvature of a patient's glenoid. While FIG. 2 shows the third surface 204 as being convex, the third surface 204 can also be concave.

The offset guide 102 can be manufactured from a variety of materials. For example, the offset guide 102 can be manufactured from a polymer, metal, ceramic, or any combination thereof. The offset guide 102 can have a unitary construction or can be manufactured from multiple components. For instance, the body 108 can be manufactured from a metal and the arcuate portion 110 can be manufactured from a ceramic. In addition, the third surface 204 can include a polymer coating.

The offset guide 102 can be manufactured using a variety of techniques. For example, the offset guide 102 can be cast, machined from a billet material, injection molded, overmolded, etc. For instance, the offset guide 102 can be cast as a rough ingot and then machined to a final shape using a water jet cutter or a computer numerically controlled (CNC) machine. The offset guide 102 also can be 3D printed. In addition, a polymer outer layer can be overmolded on the offset guide 102 to protect both patient bone and the offset guide 102.

Figure 3:
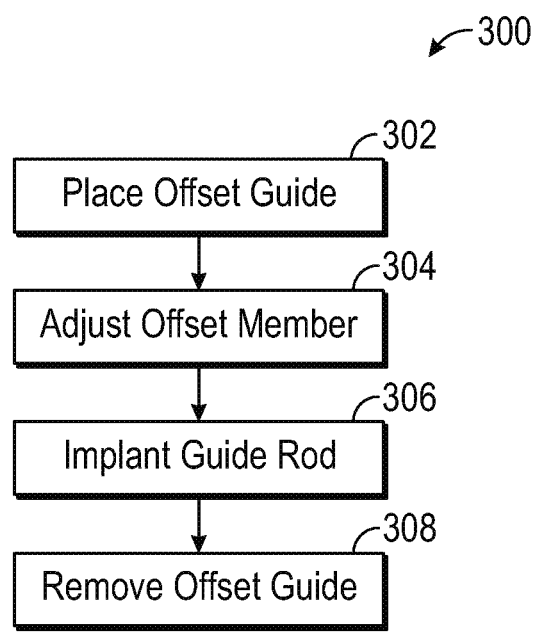
FIG. 3 shows an example method for attaching a guide rod to bone in accordance with at least one example of the present disclosure.
Figure 4:
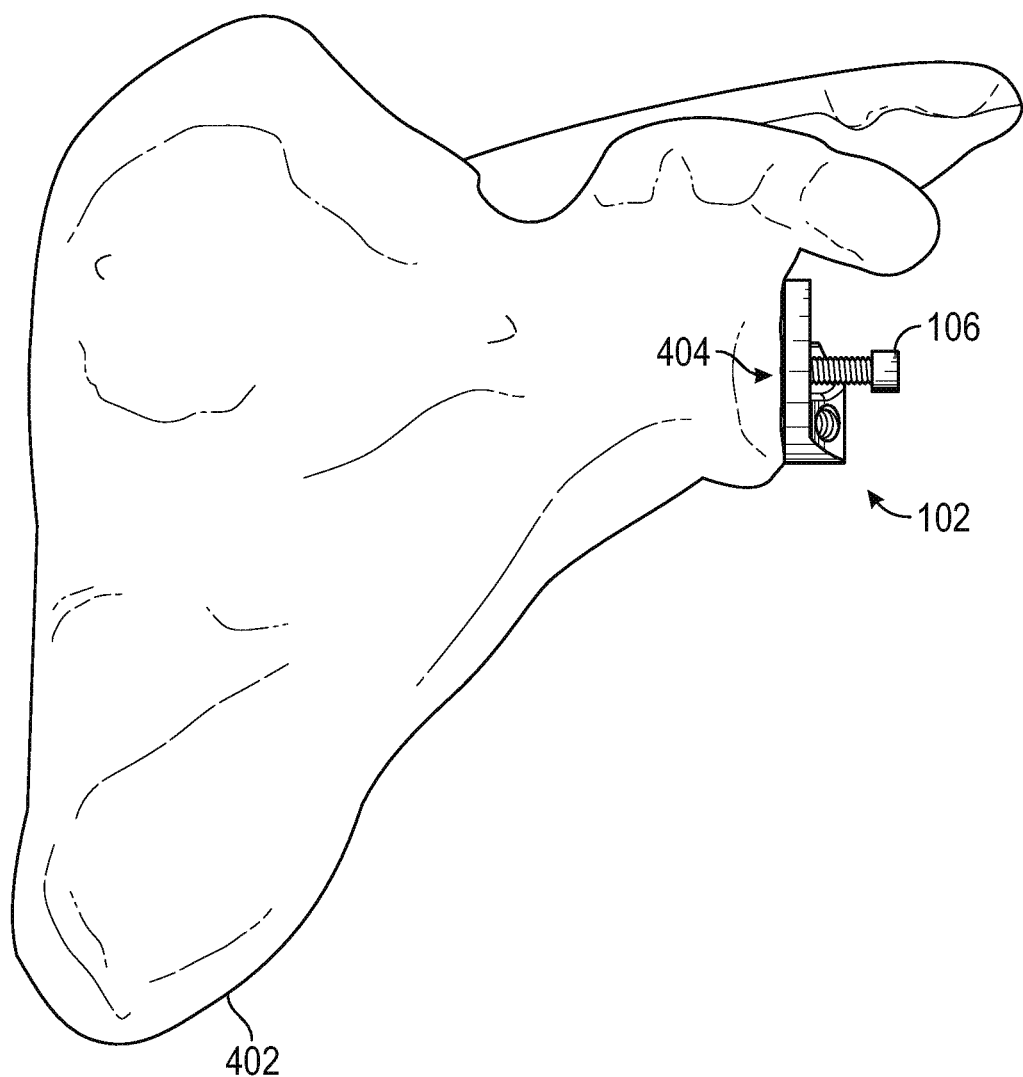
FIG. 4 shows a scapula and offset guide in accordance with at least one example of the present disclosure.

FIG. 3 shows a method 300 for attaching a guide rod to bone in accordance with at least one example disclosed herein. The method 300 begins at stage 302 where an offset guide can be placed adjacent or proximate a glenoid. For example, FIG. 4 shows an anterior view of a scapula 402. As shown in FIG. 4, the offset guide 102 can be placed adjacent or proximate a glenoid 404 such that the third surface 204 faces the glenoid 404.

Figure 5:
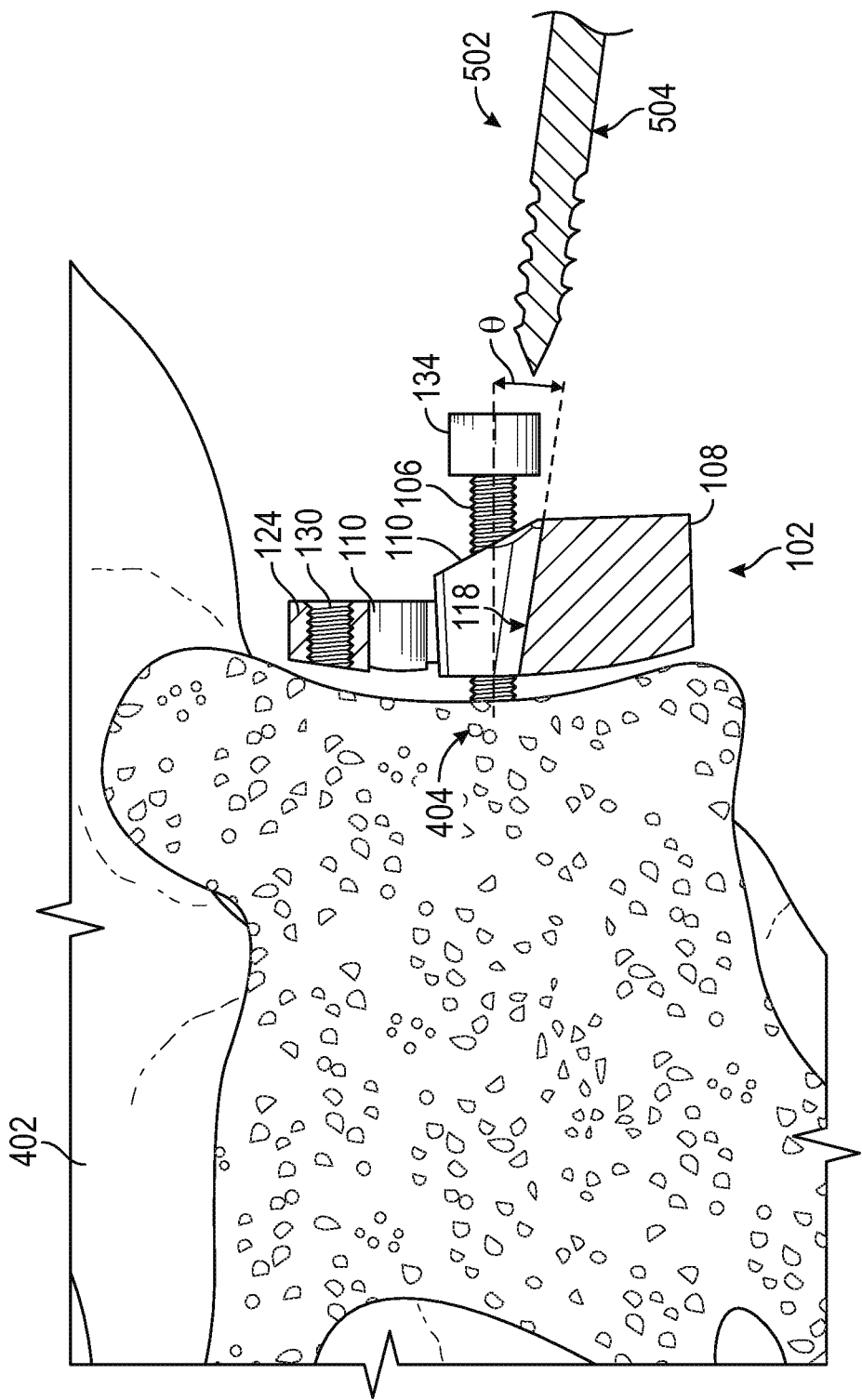
FIG. 5 shows an anterior section view of a scapula and offset guide in accordance with at least one example of the present disclosure.

From stage 302, the method 300 can proceed to stage 304 where one or more offset members can be adjusted. For example, FIG. 5 shows an inferior section view of the scapula 402. As shown in FIG. 5, the offset member 106 can be threaded into or out of the tab 124. The offset member 106 can be inserted into the tab 124 to achieve a desired offset. As disclosed herein, the offset can be patient specific or specific to a prosthesis to be implanted within the scapula 402.

Alternatively, adjustment of the offset member 106 can be accomplished before the offset guide is placed proximate the scapula 402. In addition, stages 302 and 304 can be repeated in an iterative manner until a desired offset is obtained.

While FIGS. 1, 4, and 5 show a single offset member 106, multiple offset members may be utilized during a surgery. For example, three offset members 106 can be used with the tabs 124. Each of the offset members 106 can be advanced into a respective tab 124 independently of other offset members 106. For instance, a first offset member may be advanced into a first tab a first distance and a second offset member may be advanced into a second tab a second distance. The first distance and the second distance need not be equal to one another.

The offset members 106 can rest against bone (e.g., the glenoid). The distance the offset members 106 are advanced into the tabs can define an offset distance for respective portions of the offset guide 102 relative to the bone. The use of the offset members 106 can allow a surgeon to orient the offset guide 102 such that a guide rod 502 can be implanted at a desired angle into the glenoid 404. The offset can also allow other instruments to be utilized during implanting the guide rod 502. For example, during implantation of the guide rod 502 irrigation can be provided to the glenoid 404 via the opening 120. In addition, the offset can minimize potential damage to the bone caused by vibration of the offset guide 102.

From stage 302 or stage 304, the method 300 can proceed to stage 306 where a guide rod can be implanted. For example, as shown in FIG. 5, the guide rod 502 can be passed through the opening 116 and into the glenoid 404. Upon implanting the guide rod 502, a sidewall 504 of the guide rod 502 can rest against the first surface 118. While FIG. 5 shows and the method 300 describes implanting a single guide rod, the offset guide 102 can be used to implant multiple guide rods. For example, the body 108 of the offset guide 102 can define multiple notches 120 that can be used to position guide rods.

From stage 306, the method 300 can proceed to stage 308 where the offset guide 102 can be removed. For example, after the guide rod 502 is implanted, the offset guide 102 can be removed by sliding the offset guide 102 along the guide rod 502. Once the offset guide 102 is removed, a surgeon can utilize the guide rod 502 with other surgical instruments such as a reamer.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

What is claimed is:

1. An offset guide comprising:
    a body having a longitudinal axis and a curved surface arranged at an angle relative to the longitudinal axis;
    an arcuate portion extending from the body, the body and the arcuate portion defining an opening;
    a plurality of tabs extending from the arcuate portion into the opening, each of the plurality of tabs defining an aperture;
    a first fin extending from the body; and
    a second fin extending from the body and connected to the first fin via the curved surface of the body, the second fin extending parallel to the first fin from the body,
    wherein a channel sized to receive a guide rod is defined between an inner surface of the first fin, an inner surface of the second fin, and the curved surface.

2. The offset guide of claim 1, wherein the angle is between about 5 degrees and about 20 degrees.

3. The offset guide of claim 1, wherein each of the apertures includes a threaded portion configured to receive an offset member.

4. The offset guide of claim 1, wherein the body includes a third surface that is curved to match a profile of a glenoid implant.

5. The offset guide of claim 1, wherein the body defines a connection member configured to connect to a handle.

6. A system for preparing a glenoid to receive a glenoid implant, the system comprising:
    a guide rod; and
    an offset guide comprising:
        a body having a first curved surface,
        an arcuate portion extending from the body and having a second curved surface, the body and the second curved surface defining an opening,
        a plurality of tabs extending from the second curved surface into the opening, each of the plurality of tabs defining an aperture,
        a first fin extending from the body into the opening, and
        a second fin extending from the body into the opening, the first curved surface located between the first fin and the second fin and arranged at an angle relative to a longitudinal axis of the offset guide, the first curved surface, the first fin, and the second fin defining a notch sized to receive the guide rod; and
    a plurality of offset members, each of the plurality of offset members sized to be received by at least one of the apertures defined by the plurality of tabs.

7. The system of claim 6, wherein the angle is between about 5 degrees and about 20 degrees.

8. The system of claim 6, wherein the plurality of offset members are bolts and each of the apertures includes a threaded portion configured to engage with one of the bolts.

9. The system of claim 6, wherein the body includes a third surface that is curved to match a profile of the glenoid implant.

10. The system of claim 6, further comprising a handle, the body and the handle configured to mate together.

11. The system of claim 10, wherein the body defines a first connection member and a second connection member located on an opposing side of the body, the handle configured to alternatively mate with the first connection member and the second connection member.

* * * * *